United States Patent [19]

Imai

[11] Patent Number: 5,025,389

[45] Date of Patent: Jun. 18, 1991

[54] METHOD OF ANALYZING REACTION RATE IN CHEMICAL ANALYSIS

[75] Inventor: Toshiaki Imai, Otawara, Japan

[73] Assignee: Kabushiki Kaisha Toshiba, Kawasaki, Japan

[21] Appl. No.: 296,823

[22] Filed: Jan. 13, 1989

[30] Foreign Application Priority Data

Jan. 16, 1988 [JP] Japan .................................. 63-7960

[51] Int. Cl.⁵ ............................................. G06F 15/42
[52] U.S. Cl. .................................... 364/497; 364/499; 364/569; 364/413.11
[58] Field of Search ............................ 364/497–499, 364/413.07, 413.11, 569; 73/863.01; 436/47; 356/39–42

[56] References Cited

U.S. PATENT DOCUMENTS

| | | |
|---|---|---|
| 3,832,135 | 8/1974 | Drozdowski et al. ......... 364/413.11 |
| 4,276,051 | 6/1981 | Ginsberg et al. .................... 364/497 |
| 4,308,231 | 12/1981 | Kolber et al. ........................ 364/497 |
| 4,313,735 | 2/1982 | Yamashita et al. ................. 364/498 |
| 4,318,615 | 3/1982 | Sagusa et al. ........................ 364/497 |
| 4,472,505 | 9/1984 | Manabe et al. ...................... 364/498 |
| 4,482,251 | 11/1984 | Saylor .................................. 364/498 |

Primary Examiner—Kevin J. Teska
Attorney, Agent, or Firm—Oblon, Spivak, McClelland, Maier & Neustadt

[57] ABSTRACT

The present invention relates to a method of analyzing a reaction rate in chemical analysis, in which a plurality of time region bands wherein the reaction rate is measured are set to be different in time series, a sample high in active value is calculated based on the data contained in the region band positioned forward in time series, and a sample low or normal in active value is calculated based on the data contained in the region positioned backward in the time series.

4 Claims, 4 Drawing Sheets

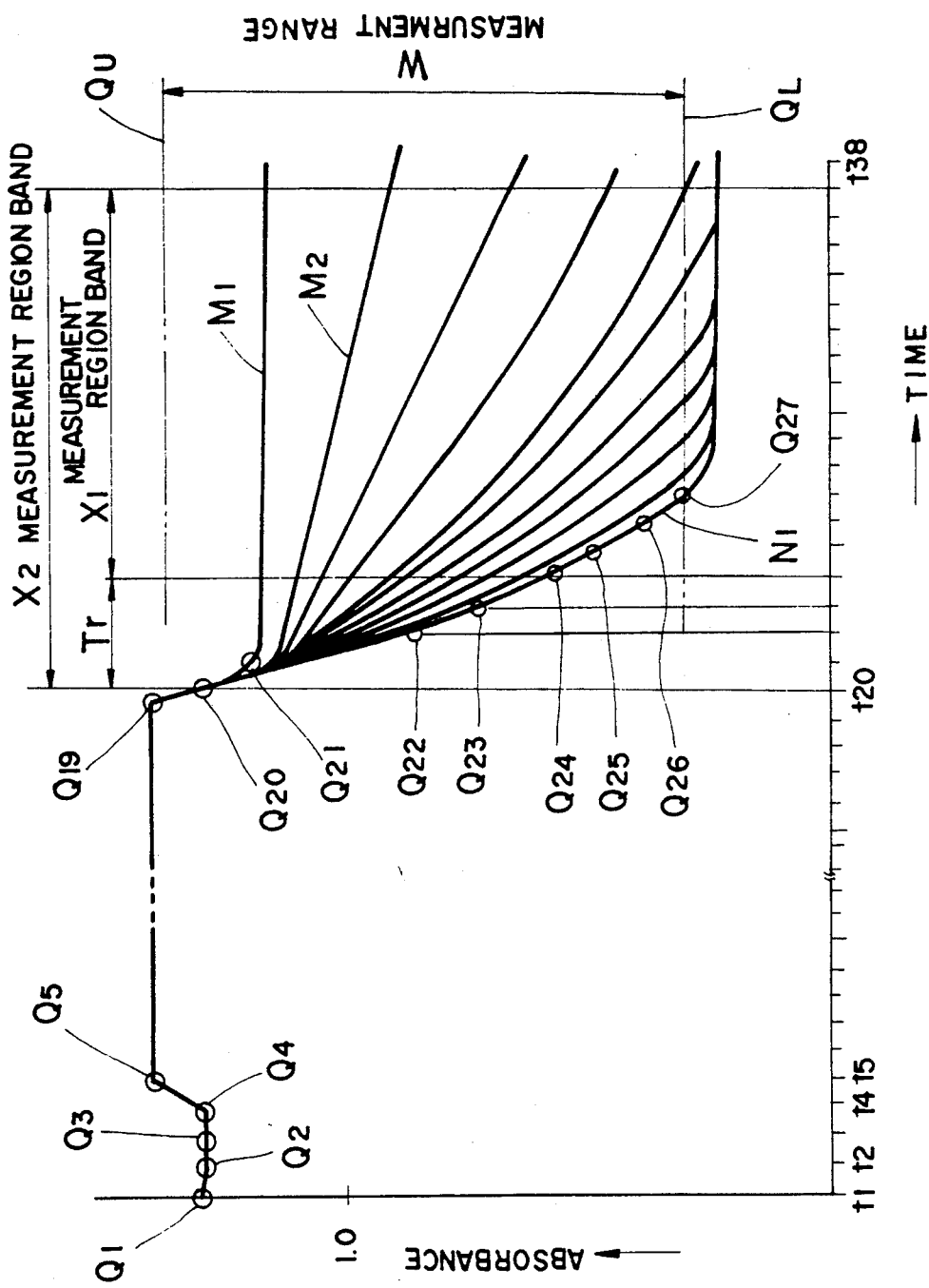

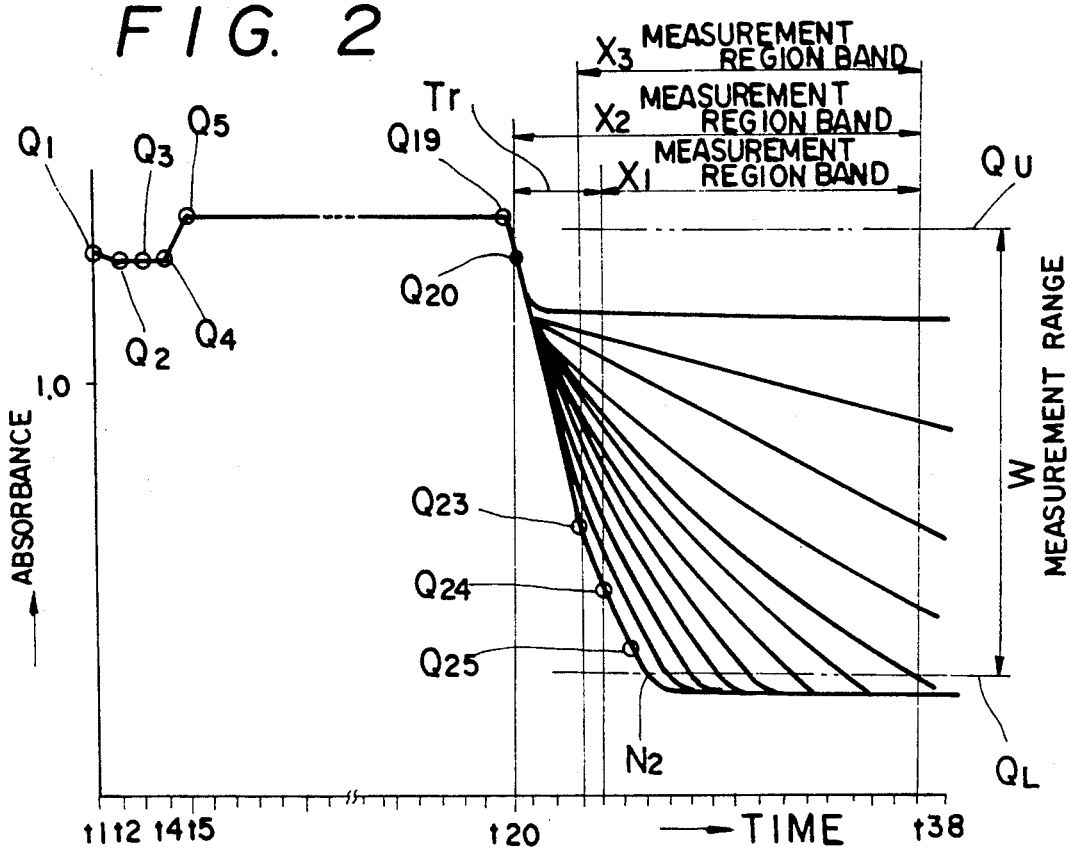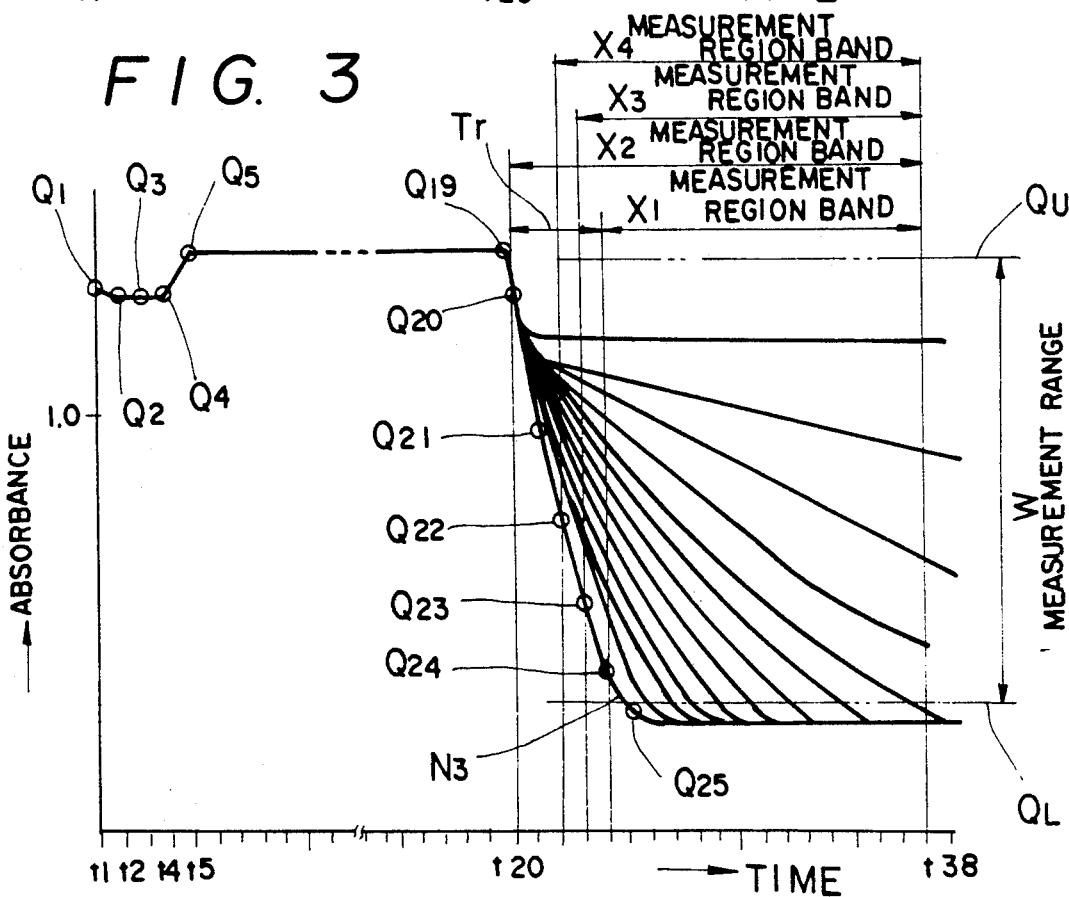

METHOD OF ANALYZING REACTION RATE IN CHEMICAL ANALYSIS

BACKGROUND OF THE INVENTION

The invention relates to improvement in a method of analyzing a reaction rate in chemical analysis used, for example, in the field of medical checks.

In modern medical diagnosis, the checks of tumors for example typically urine and blood is one of indispensable factors. In these checks, the sample to be checked and reagents are distributed into a reaction cell that is moved in a reaction tank whose temperature is kept constant, then after the reaction, the resulting liquid to be measured is illuminated by a photometric light, the absorbance is detected, and thus, for example, the active amount of an enzyme in a serum is measured. In this case, in the analytical method using a conventional reaction rate measuring process, a sample and all reagents required for measurement are mixed, and after a prescribed period of the reaction has passed, the absorbance of the reaction liquid is detected. This "prescribed period" is generally called "lag time" and this lag time has the following three meanings:

(1) The time period which goes from the time when reagents are added to the time when the change in temperature caused thereby stops.

For example, when an enzyme reaction is measured, it is required to keep the temperature constant, and therefore the value of the temperature in the reaction cell during the reaction is to be kept constant at all times. However, in the case wherein the temperature of a reagent that is added in the final stage is different from that constant temperature, since the temperature in the cell changes naturally at the time of the addition, generally the measurement is carried out taking the period required for settling of that change in temperature into consideration.

(2) The time period required for the stabilization of a reaction liquid after the stirring.

For example, after the final reagent is added, the sample and the reagent ar stirred well. At that time, a state unfavorable for the measurement of absorbance, for example, a state wherein bubbles suspend in the reaction liquid continues for a while. Consequently, for accurate measurement the system must wait until the unstable state of the reaction liquid due to the stirring, for example, the presence of bubbles in the reaction liquid disappears.

(3) Lag time of the reaction.

For example the analysis of glutamic oxaloacetic transaminase (GOT) in serum can be expressed by the following two step separate reactions (i.e. equations):

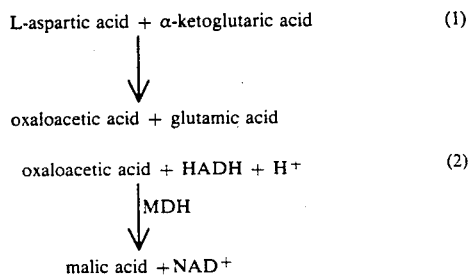

Note: MDH = malate dehydrogenase
HADH = reduction type nicotinamide dinucleotide
NAD⁺ = nicotinamide dinucleotide In the measurement of enzyme reactions by using NADH, if the reactions include the dehydrogenation reaction of the coenzyme NADH indirectly or directly, the measurement is carried out at around 340 nm. Here, the first reaction cannot be detected optically, but the produced oxaloacetic acid can be related to the second reaction thereby enabling an optical measurement.

In this case, the reduction type coenzyme (NADH) has absorption in the ultraviolet range, the change in absorbance that takes place when the NADH changes to NAD⁺ according to the equation (2) is utilized for the measurement of the enzyme active amount of the above GOT, and in order to measure that reaction, the second reaction must be waited until the first reaction proceeds. That is, the reaction according to the second reaction equation (2) is required to be waited until oxaloacetic acid is produced enough to reach the maximum rate in the conversion of NADH to NAD⁺ during the reaction of the equation (1). Generally, the lag time including this waiting time until said maximum rate is obtained is called lag time of the reaction. Accordingly, so long as the accuracy of measurement is to be as great as possible, it is required to secure a lag time that will be long enough to expect normal proceeding of reactions with respect to all factors.

Therefore, in conventional methods of measuring reaction rates, the above-mentioned lag time after the addition of all the reagents required for measurement was preset at a longest period in which reactions will proceed as prescribed, and the measured value of the absorbance during that period was excluded in the essential calculation of the measurement of the absorbance.

SUMMARY OF THE INVENTION

However, for example, in measurement of samples high in active value, since the proceeding of the reaction is high, if the lag time is preset based on the above concept, NADH required for the proceeding of the reaction disappears in the lag time. Thus, if the calculation of the measurement is carried out based on the data obtained in the measurement region band, an incorrect data will be obtained. Therefore, in conventional methods of measuring reaction rates, the reaction limit level was set based on the unit of the absorbance, and when the NADH concentration lowered below a certain level in the measurement region, an alarm or information that the particular sample was too active to be measured was issued. Accordingly, in the conventional method, it had a defect that there inevitably happened a limit on the range of the measurement, and a highly active sample could not be measured.

Taking the above situation into consideration, this invention has been completed, and the object of the present invention is to provide a novel method of analyzing a reaction rate in chemical analysis wherein a plurality of measurement region bands required for measurement of a reaction are set thereby allowing the range of measurement to be widened.

To attain the above object, first the present invention provides a method of analyzing a reaction rate in chemical analysis wherein first a sample and a reagent are reacted, and by measuring the reaction rate thereof, characteristic values such as the active value and the concentration concerning the sample to be measured are measured and analyzed, characterized in that a plurality of measurement region bands different in time series in which the said reaction rate will be measured are provided, the measurement of a sample high in active value is calculated by using data included in the region band in a forward position in said time series, and the measurement of a sample normal or low in active value is calculated by using data included in the region band in a backward position in said time series.

Secondly, the present invention provides a method of analyzing a reaction rate in chemical analysis as will be set forth below wherein first a sample and a reagent are reacted, and by measuring the reaction rate thereof, characteristic values such as the active value and the concentration concerning the sample to be measured are measured and analyzed, characterized in that a plurality of measurement region bands different in time series in which the said reaction rate will be measured are provided, the measurement of the characteristic values concerning said sample to be measured is carried out by the measurement mode that uses the region band positioned backward in said time series, and when the number of the effective measured data obtained in said measurement mode is less than a predetermined value, the analysis is automatically carried out based on the measurement mode that uses the region band positioned forward in said time series.

In the present invention, a plurality of measurement region bands different in time series are provided where data for the calculation of the reaction rate are collected, and one of the measurement region bands is a region band positioned forward in the time series, and the other is a region band positioned backward in the time series, so that the measurement of a sample high in active value can be carried out in the region band positioned forward in said time series, while the measurement of a sample normal or low active value can be carried out in the region band positioned backward in said time series, thereby extending the limit of the measurement.

BRIEF DESCRIPTION OF THE DRAWINGS

FIG. 1 is a time-absorbance change diagram illustrating a first embodiment of the present method of analyzing a reaction rate; FIGS. 2 and 3 are characteristic diagrams illustrating a second embodiment of the present invention.

DESCRIPTION OF THE PREFERRED EMBODIMENTS

Figure 4:
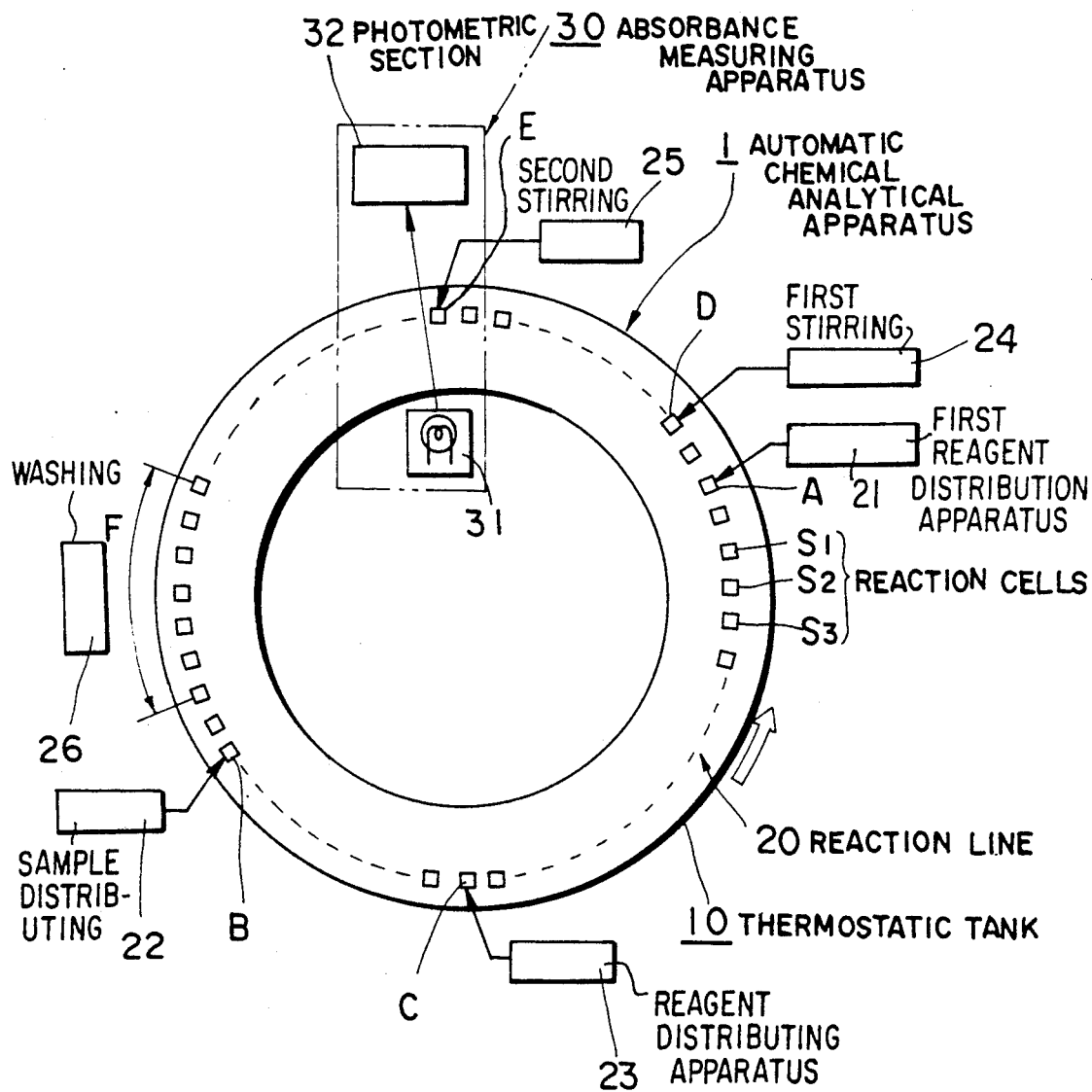
FIG. 4 is a schematic block diagram of an automatic analytical apparatus for carrying out the present method of analyzing a reaction rate.
Figure 5:
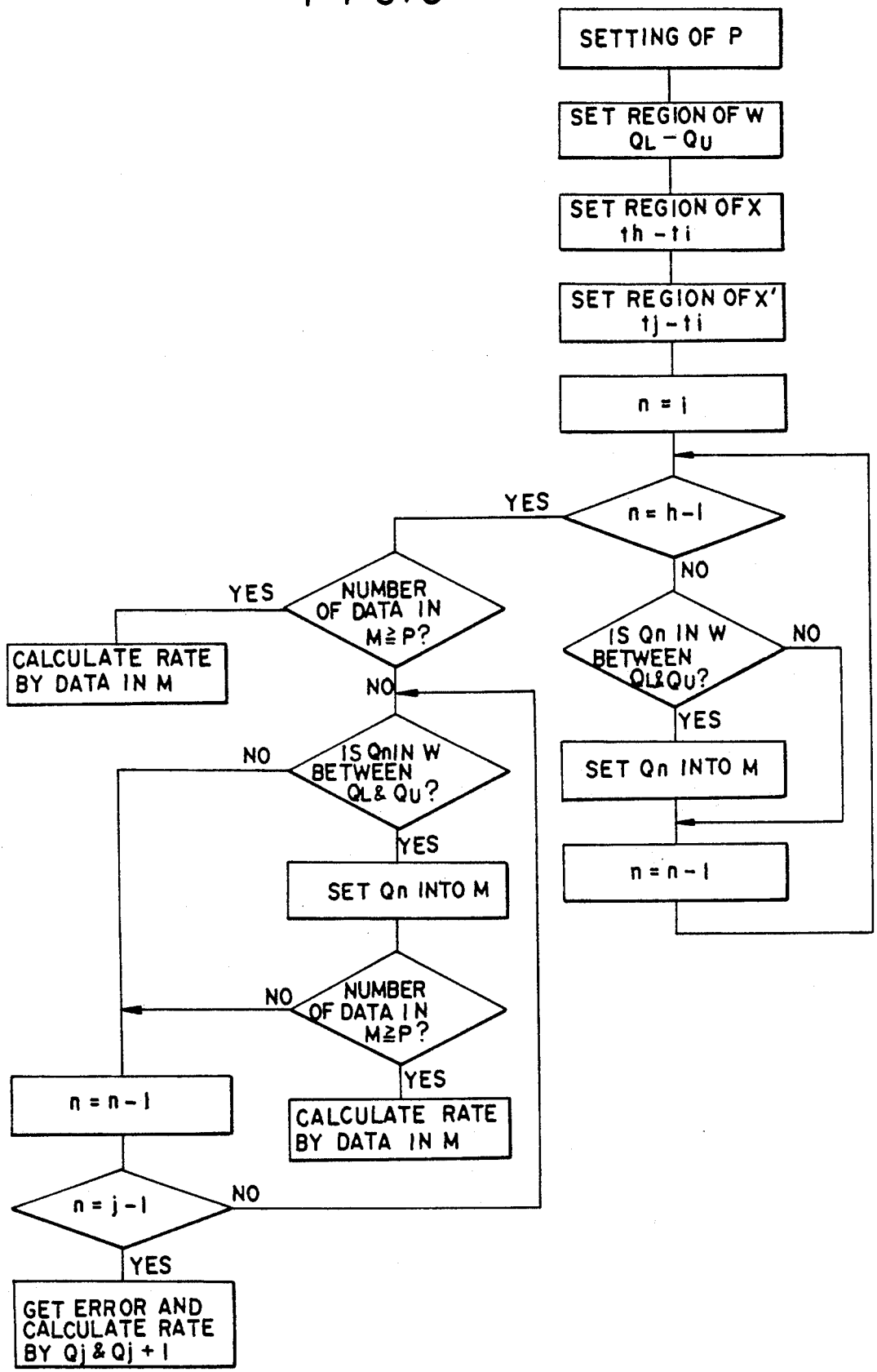
FIG. 5 is a flow chart of the calculation process.

The present invention will now be described in more detail with reference to illustrated embodiments, but before that an automatic analytical apparatus for carrying out the present method of analyzing a reaction rate is described with reference to FIG. 4.

The automatic chemical analytical apparatus designated generally 1 consists of a thermostatic tank 10 having a structure known per se, for example, in the shape of a circle, a reaction line 20 made up of reaction cells Sn (wherein n is 1 to 51) that are for example 51 in number and can be rotated in said thermostatic tank 10 in the direction shown by the arrow according t a certain principle, a first reagent distributing apparatus 21, a sample distributing apparatus 22, a second reagent distributing apparatus 23, a first stirring apparatus 24, a second stirring apparatus 25, and a suitable reaction cell washing apparatus 26 that are arranged respectively at prescribed positions A to F around said thermostatic tank 10, and a suitable absorbance measuring apparatus 30 made up of a light source lamp section 31 and a photometric section 32 with said reaction line 20 between them. In this case, said first reagent distributing apparatus 21, said sample distributing apparatus 22, said second reagent distributing apparatus 23, said first stirring apparatus 24, said second stirring apparatus 25, said reaction cell washing apparatus 26, and said absorbance measuring apparatus 30 are apparatuses of known types having functions and structures known per se respectively.

When the reaction line 20 is in the state of stop, a first reagent is distributed from the first reagent distributing apparatus 21 into the reaction cell Sn situated opposite to position A, a sample to be measured is distributed into the reaction cell Sn situated opposite to a position B from the sample distributing apparatus 22, and a second reagent is distributed from the second reagent distributing apparatus 23 into the reaction cell Sn situated opposite to a position C. Stirring of the sample and the first reagent is effected in the reaction cell Sn situated opposite to a position D by the first stirring apparatus 24, and stirring in the reaction cell Sn situated opposite to a position E is effected by the second stirring apparatus 25 after the distribution of the second reagent. After these operations have been completed, the reaction line 20 is rotated one and half rotation and ½ pitch to be moved to the next position.

In this way, during the one rotation of each reaction cell Sn through the thermostatic tank 10, the measurement of the absorbance of the reagent or the mixture liquid of the sample with the reagent contained in the cell is carried out by the action of the absorbance measuring apparatus 30. Therefore, if each reaction cell Sn is assumed to rotate one turn in the thermostatic tank 10 in, for example, 18 sec, data of the absorbance can be obtained from the mixture liquid of the sample and the reagent in the reaction cell in every 18 sec.

Now, the present method of analyzing a reaction rate that uses the automatic chemical analytical apparatus 1 having the above constitution will be described with reference to the time-absorbance change diagram shown in FIG. 1.

After a first reagent is distributed into a reaction cell Sn at the first reagent distributing position (position A) (After the time period $t_1$ has expired), the absorbance $Q_1$ is measured. Then the absorbance $Q_2$ in the amount of time ($t_2$) that the reaction line needs to rotate the reaction cell Sn to the position next to the first reagent distributing position is measured, and the absorbance $Q_3$ at the next time ($t_3$) is measured. Thus, after (time $t_4$) a sample is distributed at the sample distributing position (position B), the absorbance $Q_4$ is measured, after (time $t_5$) the stirring at the first stirring position (position D) is effected, the absorbance $Q_5$ is measured, and every time (each of time $t_6$ to time $t_{19}$) when the reaction cells Sn are rotated, each of the absorbances $Q_6$ to $Q_{19}$ of the solutions in the reaction cells Sn are measured.

After (time $t_{20}$) a second reagent is distributed at the second reagent distributing position (position C), the absorbance $Q_{20}$ is measured, after (time $t_{21}$) stirring at the second stirring position (position E) is carried out, the absorbance $Q_{21}$ is measured, and every time (each of time $t_{22}$ to time $t_{38}$) when the reaction cells Sn are rotated, each of the absorbances $Q_{22}$ to $Q_{38}$ in the reaction cells Sn is measured. All of the data of the measurements of the absorbances measured at these points are stored in suitable memory and regenerating means (not shown) such as a computer.

Under these conditions for the measurement of absorbance, the period from the time $t_{20}$ when the second reagent is distributed into the reaction cell Sn to the time $t_{23}$ is set as lag time Tr, and a measurement region band $X_1$ where the change in absorbance of a sample low in active value will be calculated is set in the region band from the time $t_{24}$ to the time $t_{38}$. A measurement region band $X_2$ where the change in absorbance of a sample high in active value is set in the region band (including the lag time band) from the time $t_{20}$ to the time $t_{38}$. In other words, the measurement time region bands $X_1$, $X_2$ are previously set such that the reaction rates can be calculated on the basis of all the absorbances from the absorbance $Q_{24}$ measured at the time $t_{24}$ to the absorbance $Q_{38}$ measured at the time $t_{38}$ in the case of a sample low in low activity, and on the basis of all the absorbances from the absorbance $Q_{20}$ measured at the time $t_{20}$ to the absorbance $Q_{38}$ measured at the time $t_{38}$ in the case of a sample high in active value. W in FIG. 1 is the previously set measurement range of absorbance, and $Q_U$ is its upper limit value and $Q_L$ is its lower limit value. $X_2$ is defined as the region band positioned forward in time series, and $X_1$ is defined as the region band positioned backward in time series.

Thus, in the case of a sample (e.g., $M_1$, and $M_2$) low in active value, since the states of changes in absorbance for time in the measurement region band X from the time $t_{24}$ to the time $t_{38}$ become approximately constant (linear), the measured values of the absorbances therein fall in the above absorbance measurement range W thereby exhibiting the measurement effect, while, in the case of a sample (e.g., $N_1$) high in active value, since major part of NADH is consumed already at the point beyond the above-mentioned lag time $t_{23}$, the values of the absorbances concerning the measurement after the time $t_{26}$ will be lower than the above-mentioned lower limit $Q_L$, and therefore the accurate measured value cannot be calculated, thereby resulting in a data error.

However, since effective data greater than the above-mentioned lower limit value $Q_L$ are in the data of the measurement of absorbances measured after the time $t_{21}$, and remain in the above-mentioned memory and regenerating means, if the effective measured data are used in the measurement of a sample high in active value, calculation of measurement accurate enough can be carried out.

The present invention has been completed with attention paid to the above point, and the present first invention is constituted such that when a sample high in active value is measured, the measurement data of absorbances measured in the measurement region band $X_2$ set in time series before the measurement region band $X_1$ for a sample low in active value are utilized.

Next, the second constitution of the present invention and its action will be described with reference to FIGS. 2 and 3.

In the case of FIG. 2, the operation of measurement of absorbance is started with the measurement mode that uses the measurement region band $X_1$ having the lag time for the case of a sample low in active value, and in the case that absorbance measured values lower than the above-mentioned lower limit $Q_L$ began to increase during the measurement, and the measurement must be carried out with the number of effective absorbance measured values (absorbance data) higher than the lower limit value $Q_L$ being, for example, only 2 (absorbance data $Q_{24}$, and $Q_{25}$ in the time $t_{24}$ and the $t_{25}$) as shown in a curve $N_2$, suitable means is used to convert that state to an electrical signal, then it is inputted into a suitable counter means or comparative means for discrimination to expand (or shift) automatically the measurement region band to a region band $X_3$ positioned forward in time series, and the calculation of the measurement is carried out on the basis of the measurement mode that uses absorption data $Q_{23}$ in the time $t_{23}$ contained in the lag time.

In FIG. 3, as shown by a curve $N_3$, in the case where the absorption data $Q_{25}$ is below the lower limit value $Q_L$, a measurement region band $X_4$ positioned further forward in time series is set, and the absorption data $Q_{24}$, $Q_{23}$, and $Q_{22}$ at the time $t_{24}$, the time $t_{23}$, and the time $t_{22}$ are incorporated from said memory and regenerating means to carry out the calculation of the measurement. In this way, the measurement region band is successively moved until the measurement region band is expanded or shifted to a region where three absorption bands $Q_{20}$, $Q_{21}$, and $Q_{22}$ of the time $T_{20}$, the time $T_{21}$, and the time $t_{22}$ can be used, and the calculation of measurement is carried out. The present second invention is constituted as mentioned above. That is, in this measurement mode, the absorbance data in the lag time initially set are successively incorporated on the basis of a certain standard, so that the measured values can be calculated by using the initial measurement data of the reaction.

As the standard for the incorporation in this case, the incorporation is successively effected so that effective absorption data may be 3 or more in the illustrated embodiment. However, various incorporation methods are possible; for example, when the absorption changes of the absorption data $Q_{24}$ and the absorption data $Q_{25}$ at the time $t_{24}$ and the time $t_{25}$ exceed a certain value, the absorption change between the absorption data $Q_{22}$ at the time $t_{22}$ contained in the lag time and the absorption data at the time $t_{23}$ and the absorption change between the absorption data $Q_{25}$ and the absorption data $Q_{26}$ positioned afterward in time series are compared, and when the compared result is below a certain ratio, the absorption data in the lag time are utilized.

Although, in the above embodiment, the absorption data $Q_{20}$, the absorption data $Q_{21}$, and the absorption data $Q_{22}$ are used as a final combination, other combination, for example, a combination of the absorption data $Q_{19}$, the absorption data $Q_{20}$, and the absorption data $Q_{21}$ including the absorption $Q_{19}$ at the time when the final reagent is absent can be used.

In the illustrated embodiment, the number of absorption $Q_n$ used in the calculation is 3, but the number may be 2 at the lowest. The present invention is not limited to the embodiments described above, but various modifications may be made without departing from the sprit and scope of the present invention. For example, in the illustrated embodiments, although the time width of the measurement region band $X_1$ in the case of a sample low in active value, and the time width of the measurement region band $X_2$ in the case of a sample high in active value are set to be different, they may be set to be the same or narrow, and the measurement region band $X_2$ of the sample high in active value may be positioned more forward in time series than the measurement region band $X_1$ of the sample low in active value. The type and the structure of the automatic chemical analytical apparatus to which the present method of analyzing a reaction rate is applied are not limited to those of the illustrated embodiments, and a suitable type and structure thereof can be used.

What is claimed is:

1. A method of analyzing a reaction rate in chemical analysis, comprising the steps of:

reacting at least one sample and at least one reagent;

first measuring at various time points the level of reaction of a sample and the reagent so as to provide a plurality of measurement region bands;

dividing each of the plurality of said measurement region bands different which have time series n which the said reaction rate is measured and stored;

finding within said measurements one of said samples high in active value by using data included in the region band in a forward position in said time series;

second measuring a sample which will have a normal or low active value; and finding an active value by using a data look up of data which was part of the measurement indicated in the region band in a backward position in said time series in relation to said forward position.

2. A method of analyzing a reaction rate in chemical analysis as claimed in claim 1 wherein said reacting and first measuring steps further comprise:

reacting a first sample and a first reagent and measuring the reaction rate thereof, characteristic values such as the active value and the concentration concerning the sample to be measured are measured and analyzed the measurement of the characteristic values concerning said sample to be measured is carried out in a measurement mode that uses the region band positioned backward in said time series, and when a number of effective measured data points obtained in said measurement mode is less than a predetermined value, an analysis of the reaction is automatically carried out based on the measurement mode that uses the region band positioned forward in said time series.

3. A method of analyzing a reaction rate in chemical analysis as claimed in claim 1, wherein one of the plurality of the measurement region bands different in time series is a region band including a lag time and the other is a region band not including the lag time.

4. A method of analyzing a reaction rate in chemical analysis as claimed in claim 1 or 2, wherein the selection of the region band to be used of the plurality of the measurement region bands is decided by a manual operation.

* * * * *